United States Patent [19]

Saito et al.

[11] 4,356,072
[45] Oct. 26, 1982

[54] ISOELECTRIC POINT MARKER

[75] Inventors: Hiraku Saito, Osaka; Isamu Takagahara, Kawanishi; Yasuo Suzuki, Suita; Tuyosi Fujita, Suita; Katsumi Fujii, Suita; Takekazu Horio, Takatsuki, all of Japan

[73] Assignee: Oriental Yeast Company, Tokyo, Japan

[21] Appl. No.: 217,917

[22] Filed: Dec. 18, 1980

Related U.S. Application Data

[63] Continuation-in-part of Ser. No. 41,190, May 21, 1979, abandoned.

[30] Foreign Application Priority Data

May 31, 1978 [JP] Japan .................................. 53-64357

[51] Int. Cl.³ .............................................. B01D 57/02
[52] U.S. Cl. .................................. 204/180 G; 252/408; 260/112 R; 260/113; 260/115
[58] Field of Search .................... 260/112 R, 113, 115; 252/408; 204/180 G

[56] References Cited

U.S. PATENT DOCUMENTS 3,712,865  1/1973  Evans .................................. 252/312
3,764,711  10/1973  Melnychyn ........................ 426/201
4,107,014  8/1978  Suzuki .............................. 204/180 R

OTHER PUBLICATIONS

Chem. Abs. 69: 57372b 69: 83978y.
H. Svensson Arch Biochem and Biophys, Supplement 1, 132–138 (1962).
Lewin Analy. Biochem. 43 394–400, 1971.
Bosshard, Experimentia vol. 32, No. 6 (1976) p. 766.

Primary Examiner—Allan Lieberman
Assistant Examiner—P. Short
Attorney, Agent, or Firm—Browdy and Neimark

[57] ABSTRACT

A group of compounds having the following general formula can be obtained by reacting chromoprotein and organic acid:

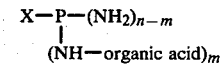

wherein X is a chromophore, P is a protein, $NH_2$ is mainly ε-amino group of lysine, n is a positive integer of 1 to 18, and m is a positive integer in the relation of $m \leq n$. This compound group has one to eighteen organic acids bonded thereto, and shows various isoelectric points in accordance with the number of the organic acids, but the respective isoelectric points are maintained constant. If such compounds each having an individual isoelectric point, are used as isoelectric point markers, it is possible to recognize accurately the position of isoelectric point only by a visual operation.

8 Claims, 3 Drawing Figures

ISOELECTRIC POINT MARKER

CROSS REFERENCE TO RELATED APPLICATION

The present application is a continuation-in-part of U.S. application Ser. No. 41,190, filed May 21, 1979, now abandoned, the entire contents of which are hereby incorporated by reference.

FIELD OF THE INVENTION

The present invntion relates to a novel isoelectric point marker and a novel method of isoelectric point determination, and more particularly to an isoelectric point marker composed of chromoprotein treated with organic acid anhydride.

BACKGROUND OF THE INVENTION

Recently, in the fields of biochemistry and clinical inspection, attention has been paid to gel isoelectric separation (also referred to as gel isoelectric focusing or gel isoelectric fractionation) as a means of separation, purification and analysis of protein. This method has been thought of as a simplified version of the density gradient isoelectric separation developed by Svenseon et al. Namely, when a mixture of special amphoteric electrolytes having an isoelectric point at various pH values is enclosed in a gel, such as acrylamide or agar, etc., and electrodes are provided at both ends of the enclosure, and electricity is passed therebetween, a pH-gradient derived from the amphoteric electrolytes is produced between both electrodes. The present invention is based on the principle that protein can be focused to the position of the isoelectric point in the pH-gradient produced by use of such an amphoteric electrolyte mixture. According to the method (C. W. Wringley: "Methods in Enzymology", Vol. 22, p559–564, Academic Press), it is, of couse, possible to isolate and purify proteins by the difference of their isoelectric points and also to obtain the isoelectric point of protein by measurement of pH-gradient in a gel, and therefore it has also a large value of utilization for a method of analyzing protein.

However, this method as the drawback that in order to measure the pH-gradient formed in a gel, there is required a complicated process comprising taking out the gel immediately after the electrophoresis, cutting it into as thin slices as possible at uniform intervals, extracting the amphoteric electrolyte existing in the respective gel slices by use of decarboxylated pure water, and then measuring pH of the respective extract. However, this method for pH measurement has difficulties in practical use such that it takes a long time to extract the amphoteric electrolyte and the cutting of the gel is difficult and poor in accuracy and, as well, pH values may fluctuate in accordance with the extraction conditions. Various ways have been tried heretofore, such as a method in which, in isoelectric separation, with respect to coloring matter of amphoteric electrolyte, by utilizing it as pH-indicator, electrophoresis is made together with a sample (A. Conway-Jacobs and L. M. Lewin: *Analytical Biochemistry*, vol. 43, p394–400, 1971), and a method in which in a similar object phenanthroline and iron complex are used (E. T. NAKHLEH et al.: *Analytical Biochemistry*, vol. 49, p218–224, 1972). However, these substances have drawbacks such that since these substances are low molecular weight compounds, diffusion takes place rapidly and also since the dissociation constants of dissociation groups at both ends of the isoelectric point values are far apart from each other, the separation layer spreads.

SUMMARY OF THE INVENTION

The inventors have sought a superior isoelectric point marker, namely an isoelectric point marking material, in order to eliminate the difficulties of pH measurement in such a gel isoelectric separation, thus resulting in completion of the present invention.

The present invention is an isoelectric point marker composed of chromoprotein treated by organic acid anhydride and having one of the following general formulas.

(1) An isoelectric point marker composed of a compound shown in the following general formula:

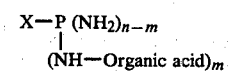

wherein
X is a chromophore,
P is a protein,
$NH_2$ is ε-amino group mainly derived from lysine,
n is a positive integer of 1–18, and
m is a positive integer in the relation of $m \leq n$.

(2) An isoelectric point marker composed of a compound having the following general formula:

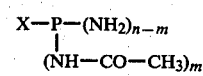

which is obtained by acetylation of the compound shown in the above general formula (1).

(3) An isoelectric point marker composed of a compound having the following general formula:

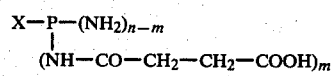

which is obtained by succinylation of the compound shown in the above general formula (1).

(4) An isoelectric point marker composed of a compound having the following general formula:

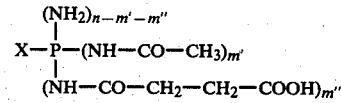

which is obtained by acetylation and succinylation of the compound shown in the above general formula (1).

Within each general formula the compound with each individual value of m (or m' and m") have different fixed isoelectric points. A plurality of such compounds with fixed isoelectric points may then be combined to produce an isoelectric point marker having a known number of fixed known isoelectric points. When added to a gel and subjected to gel isoelectric separation, colored bands are formed in the gel at each of the specific isoelectric point positions in the gel corresponding to the known isoelectric points in the marker. It is thus possible to easily determine the pH-gradient in the gel from a perusal of the position of the known isoelectric points.

DETAILED DESCRIPTION OF PREFERRED EMBODIMENTS

Figure 1:
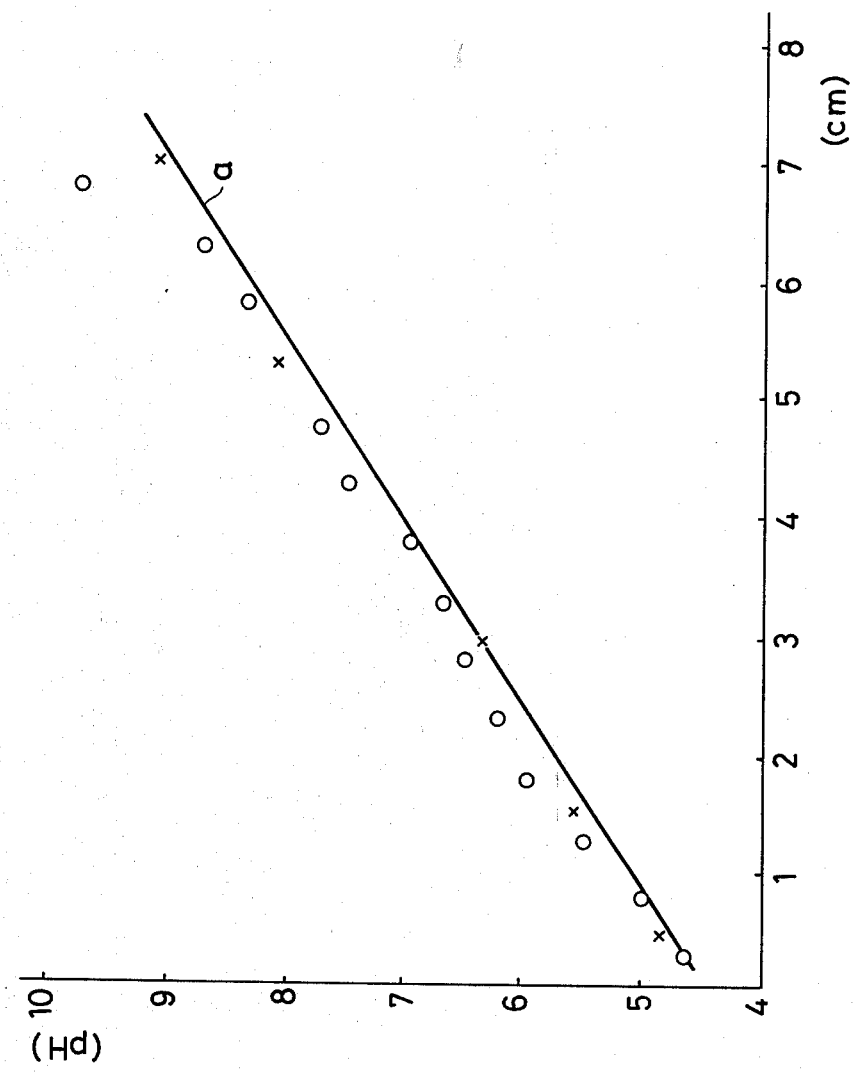
FIG. 1 is a graph for comparison of pH-gradient determined by 5 mm slices according to the prior art method as compared to the pH-gradient determined by visual observation using the isoelectric point marker of the present invention from Practical example 1, wherein a shows the pH-gradient of the pI marker, o being pH measuring points determined by the prior art method, and x being pH measuring points determined using the isoelectric point markers according to the present invention.

A raw material for producing the isoelectric point marker of the present invention is a chromoprotein, and such substances are exemplified by the following, derived from various animals and vegetables or microorganisms: cytochrome c group, myoglobin, hemoglobin, flavin protein, copper protein and so forth.

Table 1 shows representative examples of these chromoproteins.

TABLE 1

| Kind, Type of Protein | Origin | Isoelectric Point at 0-2° C. |
|---|---|---|
| Cytochrome c of oxidized type | Horse | 10.6 |
| Cytochrome $c_2$ of reduced type | Rhodopseudomonas palustris | 10.0 |
| Myoglobin | Sperm whale | 8.1 |
| Hemoglobin | Rat | 7.5 |
| Myoglobin | Horse | 7.3 |
| Cytochrome $c_2$ of reduced type | Rhodospirillum rubrum | 6.2 |
| Cytochrome $c_2$ of reduced type | Rhodopseudomonas spheroides | 5.8 |
| Cytochrome c' of oxidized type | Rhodospirillum rubrum | 5.6 |
| Cytochrome c' of oxidized type | Rhodopseudomonas spheroides | 5.0 |
| Cytochrome c-551 of oxidized type | Pseudomonas aeruginosa | 4.7 |

These chromoproteins are treated by use of organic acid anhydride. As examples of organic acid anhydrides which may be used there are acetic anhydride, propionic anhydride, butyric anhydride, succinic anhydride, malonic anhydride, etc.

The reaction is initiated by adding a certain amount of the organic acid anhydride to an aqueous solution of a certain concentration of the chromoprotein and gently stirring the solution. As the reaction proceeds, free organic acid and hydrogen ion are generated, and therefore the solution is neutralized by an alkali such as caustic soda and so forth, to permit the reaction to be sufficiently carried out under the neutral condition. The reaction is completed after 5 to 30 min. and the solution obtained from the above reaction is then separated and purified by means of an ion exchanger, thereby obtaining a plurality of isoelectric point markers having various specific isoelectric points.

The isoelectric point marker composed of a mixture of a plurality of the thus obtained organic acid anhydride treated chromoproteins according to the present invention, each of the plurality having a known isoelectric point, forms a colored band at each of the specific isoelectric point positions in the gel when subjected to gel isoelectric separation together with a sample according to the known prior art method. The position of these colored bands can be determined at a glance without conducting complicated operations, and thus it is possible to easily determine a pH-gradient in the gel from both the respective known isoelectric points and their position.

The analysis of protein by use of such an isoelectric point marker is carried out as follows. In the case that the isoelectric point of a test protein is known, the position of the intended protein can immediately be determined from the pH-gradient in the gel previously obtained by use of an isoelectric point marker of the present invention, and therefore a portion at the determined position may be taken out and the necessary measurements carried out on said portion. Also, in the case of measurement of an isoelectric point of a protein whose isoelectric point is unknown, a pH-gradient of the gel is obtained by use of an isoelectric point marker in accordance with the present invention, and on the other hand the gel is taken out and color is formed by use of a color former or the gel is sliced at certain intervals and the activity of protein in each sliced section is measured and so forth, thereby determining the position of the protein, and the thus determined position is applied to the pH-gradient obtained by an isoelectric point marker.

In the case that gels of the same composition are subjected to isoelectric separation under the same conditions, since it is thought that the pH-gradient is produced in a similar way in any of the gels, it is not always necessary for the isoelectric point marker to flow together with the sample, and it may also be allowed that isoelectric point marker alone is separately subjected to electrophoresis in an identical gel. This is particularly convenient when a number of samples are desired to be measured simultaneously.

As explained above, if the isoelectric separation of protein is carried out by use of the isoelectric point marker of the present invention, the measurement of the isoelectric point is remarkably simplified. This gives an advantage that many samples can be treated in a short time as well or decreasing the possibility of denaturation of protein during pH-measurement, so that the protein activity can be measured more accurately, resulting in a further propagation of the gel isoelectric separation in many fields.

PRODUCTION EXAMPLE 1

A 2 mM aqueous solution of cytochrome c derived from a horse heart was prepared, and acetic anhydride was added so that the final concentration thereof was from 2 mM to 360 mM. Each reaction medium containing 2 mM, 10 mM, 41 mM, 81 mM, 204 mM and 360 mM of acetic anhydride was respectively allowed to react at room temperature for 15 min. as it was stirred gently. The reactions were carried out under neutral condition as the media were neutralized with 1 N NaOH during the reaction. The reaction proceeds according to the following reaction scheme:

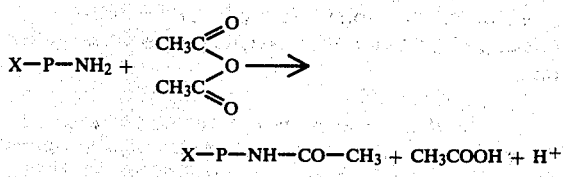

wherein X-P denotes cytochrome c.

One molecule of cytochrome c has eighteen lysine $NH_2$ groups, which can react with acetic anhydride. In the reaction, the number of lysine $NH_2$ groups which are reacted is initiated in accordance with the concentration of the acetic anhydride, and when the concentration of acetic anhydride becomes 360 mM, all the lysine $NH_2$ groups are acetylated. The acetylation number differs according to each concentration of acetic anhydride, and also even by using an identical concentration, several kinds of cytochrome c having different acetylation numbers can be obtained.

For example, in the case of using 2 mM cytochrome c, when acetic anhydride of the final concentration of 2 mM was added thereto, cytochrome c with one of the amino groups from lysine having been acetylated, and cytochrome c with two thereof having been acetylated, and cytochrome c with three thereof having been acetylated were respectively produced, and in the case of addition of 360 mM acetic anhyride, six, seven and twelve of amino groups of lysine had respectively been acetylated.

Each reaction medium was purified by ion-exchange chromatography and sucrose density gradient isoelectric separation, and thereby nine separate kinds of acetylated cytochrome c, respectively having isoelectric points of 3.9, 4.1, 4.9, 5.6, 6.5, 8.1, 9.1, and 10.2, were obtained.

PRODUCTION EXAMPLE 2

A 2 mM aqueous solution of cytochrome c originating from a horse heart was prepared, and succinic anhydride was added, so that the final concentration thereof was from 2 mM to 360 mM. Each reaction medium containing 2 mM, 90 mM, 180 mM, 270 mM and 360 mM of succinic anhydride was respectively allowed to react at room temperature for 15 min. as it was stirred gently. The reactions were carried out under neutral condition as the media were neutralized with 1 N NaOH during the reaction. The reaction proceeds according to the following reaction scheme.

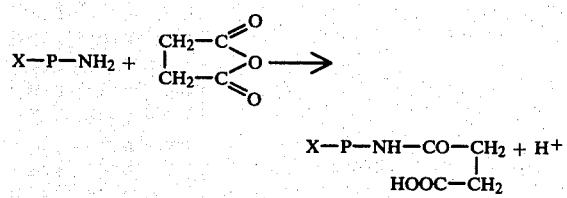

wherein X-P denotes cytochrome c.

One molecule of cytochrome c has eighteen lysine $NH_2$ groups, and in the reaction with succinic anhydride, the number of $NH_2$ groups which are reacted is initiated in accordance with the concentration of succinic anhydride, and when the concentration of succinic anhydride becomes 360 mM, all eighteen of the lysine $NH_2$ groups are entirely succinylated. The succinylation number differs according to each concentration of succinic anhydride, and also even by using an identical concentration, several kinds of succinylated cytochrome c having different succinylation number can be obtained.

For example, in the case of 2 mM cytochrome c, when succinic anhydride of the final concentration of 2 mM was added thereto, ones having isoelectric point of 10.2 and 9.4 were respectively obtained, and in the case of addition of 6 mM succinic anhydride, ones having isoelectric point of 10.2, 9.4 and 7.5 were respectively obtained, and in the case of addition of 18 mM succinic anhydride, ones having isoelectric point of 10.2, 9.4 and 7.5 were respectively obtained, and in the case of addition of 30 mM succinic anhyride, ones having isoelectric point of 9.4, 7.5 and 6.6 were respectively obtained, and in the case of addition of 64 mM succinic anhydride, ones having isoelectric point of 9.4, 7.5, 6.6 and 5.4 were respectively obtained, and in the case of addition of 360 mM succinic anhydride, ones having isoelectric point of 5.4 and 4.1 were respectively obtained.

Each reaction medium was purified by ion-exchange chromatography and sucrose density gradient isoelectric separation, and thereby nine separate kinds of succinyl cytochrome c respectively having isoelectric point of 3.9, 4.2, 4.5, 5.0, 5.6, 6.0, 7.8, 9.5 and 10.2 were obtained.

PRACTICAL EXAMPLE 1

1.2 g of acrylamide, 60 mg of N,N'-methylenebisacrylamide, 0.012 mg of riboflavin, 0.135 ml of N,N,N',N'-tetramethylethylene diamine, 5 mg of ammonium persulfate and 1.2 ml of 40% Ampholine (pH 3.5-10) (Trade name, made by LKB Co., Sweden) was dissolved in pure water and brought to 24 ml. This solution was sufficiently mixed together in a flask, and after the deairing thereof in a suction desiccator, it was charged in a glass column (5×100 mm) up to about 70 mm, and photopolymerization was carried out and thus a gel for isoelectric separation was prepared.

On the other hand, as isoelectric point markers, a combination of five of the separate kinds of acetylated cytochrome c having isoelectric points respectively of 4.9, 5.6, 6.5, 8.1 and 9.5 obtained by Production Example 1 was provided.

EDTA, mercaptoethyl alcohol and Tris-HCl buffer of pH 7.5 were added to the liver of a rat, and the mixture was ground and centrifuged at 105,000×g thereby obtaining a supernatant liquid. 14 ml of said supernatant liquid (corresponding to 7 mg of the liver) was used as a sample, to which was added 10 ml of the combined solution containing 20 mg of each said isoelectric point marker acetylated cytochome c and 24 ml of 60% glycerine solution (Ampholine concentration 4% of Ampholine (pH 3.5-10), and the resulting mixture was quietly poured onto said gel thereby preparing a sample layer. On this sample layer 50 ml of a protective layer composed of 15% glycerine and 2% Ampholine (pH 3-6) was overlaid.

The lower end of the sample gel thus obtained was dipped in a catholyte composed of 1 M NaOH aqueous solution, and the upper end thereof was dipped in an anolyte composed of 0.02 M phosphoric acid aqueous solution, and electricity was passed between the lower and upper ends at a constant voltage of 200 v for five hours. During this passage of electricity, the temperature of the column was maintained at a temperature of 0°–1° C. by means of cooling water.

After stopping the pass of electricity, the gel was taken out of the column, the position of isoelectric point marker was detected by the naked eye, and on the other hand, the gel was sliced to obtain pieces of 5 mm in breadth, and Ampholine was extracted by use of 0.5 ml of water, and pH was respectively measured, and a pH-gradient diagram was made from each said position and isoelectric point.

The result thereof is shown in FIG. 1 from which it is clear that the pH-gradient formed by use of the prior art 5 mm-slicing method and the pH-gradient formed by the visual observation by use of the isoelectric point marker of the present invention coincide well.

Moreover, each of the pieces sliced into fourteen equal pieces at intervals of 5 mm was added with 0.6 ml of 0.1 M Tris-HCl buffer containing 10 mM EDTA and 20 mM 6-mercaptoethyl alcohol and then homogenized. This homogenized liquid was centrifuged at 3000×g for 15 min., and the pyruvate-kinase activity of the resulting supernatant liquid was measured.

Figure 2:
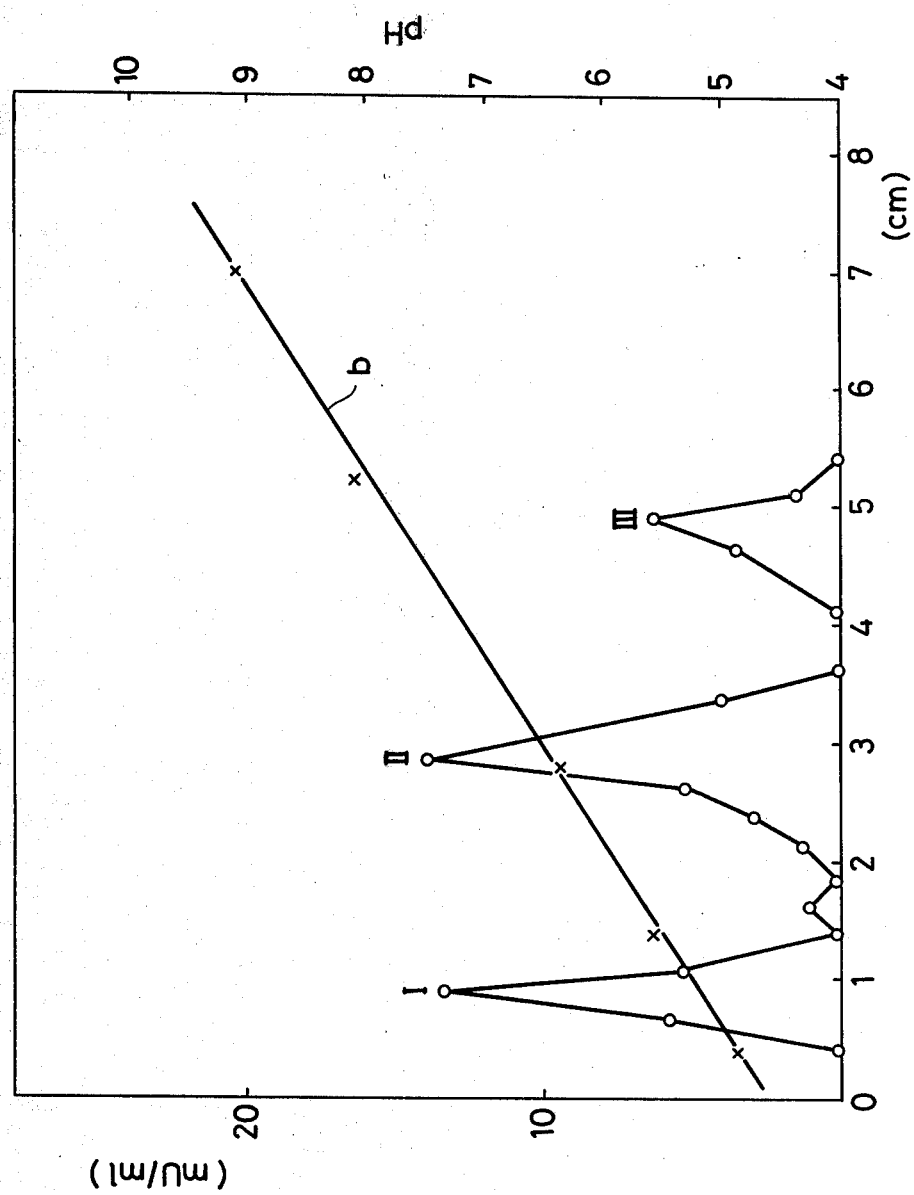
FIG. 2 is a graph showing the separation of the pI-marker of the present invention from Practical example 1 and the isoenzyme separation of pyruvate kinase, wherein b shows the pH-gradient of the pI marker, I being L-type pyruvate kinase, II being L-type pyruvate kinase, and III being S-type pyruvate kinase.

As shown in FIG. 2 showing the result, the pyruvate-kinase of rat liver was separated into three isoelectric point isoenzymes and the isoelectric points were obtained from positions showing each active peak, with the result that the respective value of 1 (pI=4.9), 2 (pI=6.2) and 3 (pI=7.8), placing in order from the lower one, were obtained.

PRACTICAL EXAMPLE 2

Quite like Practical Example 1, pI isoenzyme pattern of pyruvate kinase of normal rat and tumor-bearing rat (inoculated with Rhodamine-sarcoma) were inspected. The cutting at the time of measurement was roughly performed centering around the positions of pH 4.9=L-type, pH 6.2=L-type, pI 7.8=S-type according to the pH-gradient obtained from the pI marker, and thus the measurement was carried out.

Figure 3:
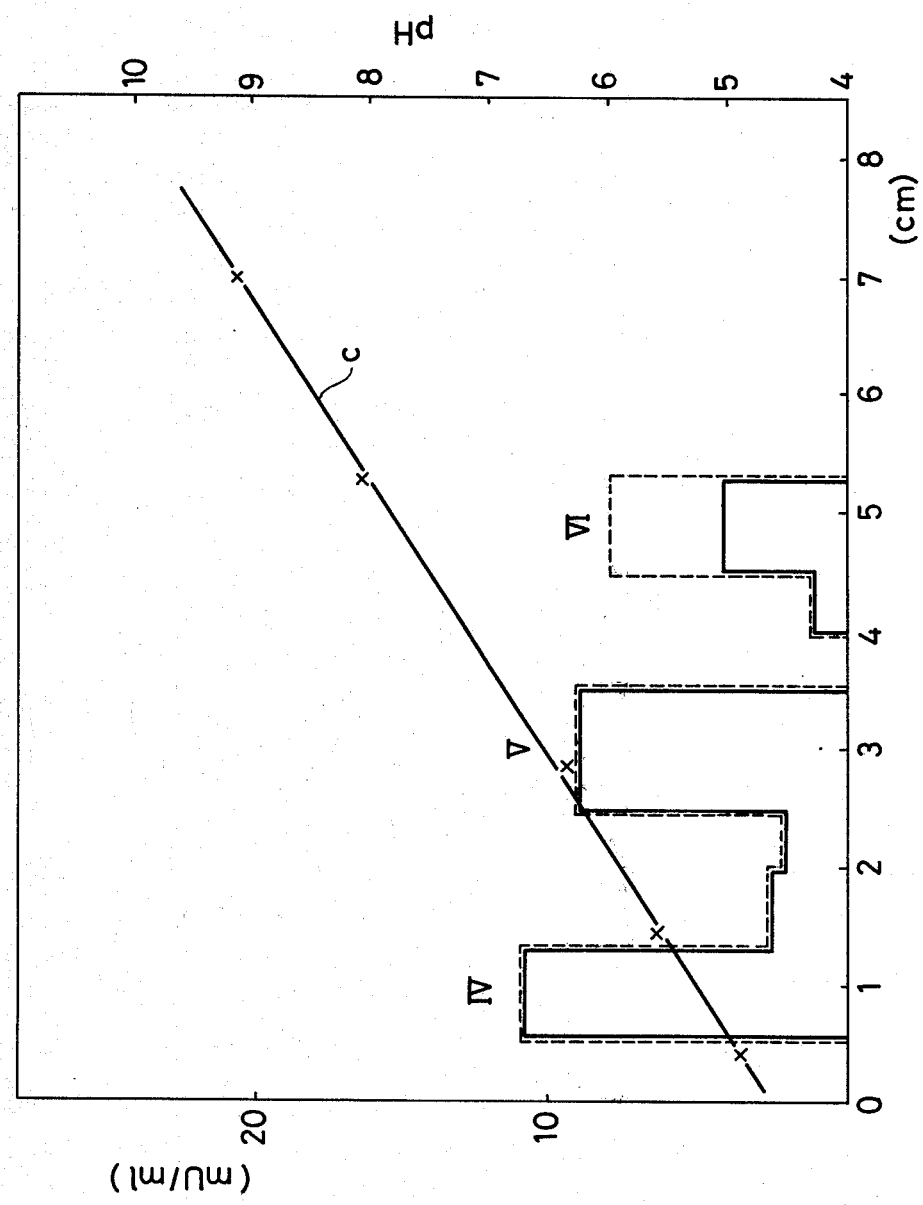
FIG. 3 is a graph showing the pI isoenzyme pattern of pyruvate kinase of normal rat and tumor-bearing rat liver by use of the pI marker of the present invention, wherein c shows the pH-gradient of the pI marker, IV being L-type pyruvate kinase, V being L-type pyruvate kinase, and VI being S-type pyruvate kinase, the solid line showing normal rat and the broken line showing tumor-bearing rat.

The result is shown in FIG. 3, wherein c denotes the pH-gradient of the pI marker, IV denotes the detection amount of L-type pyruvate kinase, V denotes that of L-type pyruvate kinase, and VI denotes that of S-type pyruvate kinase. The solid line shows those of the normal rat, and the broken line shows those of the tumor-bearing rat.

From this drawing it is apparent that by use of the pI marker of the present invention it is possible to easily detect the fact that in the case of the tumor-bearing rat S-type pyruvate kinase was increased abnormally.

It will be obvious to those skilled in the art that various changes may be made without departing from the scope of the invention and the invention is not to be considered limited to what is described in the specification.

What is claimed is:

1. An isoelectric point marker, comprising a mixture of a predetermined number greater than 2 of separated and purified compounds comprised cytochrome c acetylated or succinylated by 1–18 acetyl or succinyl groups, wherein both groups may be present on the same compound, and wherein each compound of said mixture is a single purified compound having a known type and number of said acetyl or succinyl groups, and therefore a single known isoelectric point, and wherein each said compound in said mixture is present in a predetermined amount.

2. An isoelectric point marker in accordance with claim 1, wherein all of said groups are acetyl groups for each of the compounds of said mixture.

3. An isoelectric point marker in accordance with claim 1, wherein all of said groups are succinyl groups for each of the compounds of said mixture.

4. An isoelectric point marker in accordance with claim 1, wherein both acetyl and succinyl groups are present on at least one of the compounds of said mixture.

5. An isoelectric point marker in accordance with claim 1, wherein each of said compounds are present in said mixture in substantially equal amounts.

6. An isoelectric point marker in accordance with claim 1, wherein said cytochrome c is horse heart cytochrome c.

7. In the method of gel isoelectric separation comprising passing electricity through an isoelectric separation gel to produce a pH-gradient therein, the improvement comprising adding the isoelectric point marker in accordance with claim 1 to said gel prior to the step of passing electricity therethrough, whereby, after said step of passing the electricy therethrough, colored bands are formed in said gel at the isoelectric point of each of the compounds in said marker.

8. The isoelectric separation gel having the isoelectric point marker in accordance with claim 1 therein.

* * * * *